(12) United States Patent
Kretschmer

(10) Patent No.: US 6,858,558 B2
(45) Date of Patent: Feb. 22, 2005

(54) OLEFIN POLYMERIZATION CATALYST COMPONENT AND CATALYST SYSTEM AND POLYMERIZATION PROCESS USING SUCH A CATALYST SYSTEM

(75) Inventor: Winfried Peter Kretschmer, Groningen (NL)

(73) Assignee: Stichting Dutch Polymer Institute, Eindhoven (NL)

( * ) Notice: Subject to any disclaimer, the term of this patent is extended or adjusted under 35 U.S.C. 154(b) by 0 days.

(21) Appl. No.: 10/469,832

(22) PCT Filed: Mar. 5, 2002

(86) PCT No.: PCT/NL02/00145

§ 371 (c)(1),
(2), (4) Date: Mar. 23, 2004

(87) PCT Pub. No.: WO02/070569

PCT Pub. Date: Sep. 12, 2002

(65) Prior Publication Data

US 2004/0192541 A1 Sep. 30, 2004

(30) Foreign Application Priority Data

Mar. 5, 2001 (WO) .............................. PCT/NL01/00179

(51) Int. Cl.$^7$ .................................................. C08F 4/64
(52) U.S. Cl. ...................... 502/155; 502/103; 502/120; 502/155; 502/167; 526/129; 526/130; 526/160; 526/165; 526/161; 526/172; 526/943

(58) Field of Search ................................. 502/103, 155, 502/120, 167; 526/129, 130, 160, 161, 165, 172, 943

(56) References Cited

U.S. PATENT DOCUMENTS 6,420,300 B1 * 7/2002 McMeeking et al. ....... 502/155

FOREIGN PATENT DOCUMENTS

WO             99/14250         3/1999

* cited by examiner

Primary Examiner—Caixia Lu
(74) Attorney, Agent, or Firm—Browdy and Neimark, P.L.L.C.

(57) ABSTRACT

The invention relates to a catalyst component and a catalyst system for the preparation of high molecular weight ethylene or alpha-olefin homopolymers, ethylene-alpha-olefin copolymers, terpolymers or tetrapolymers, in a polymerization process, which is expediently effected in solution, at elevated temperature, preferably at least 80 DEG C. The catalyst system comprises a group 4–6 metal, preferably group 4 metal, a cyclic ligand (such as a cyclopentadienyl-type ligand), which forms a delocalized pi-bond with the metal M, a monohapto bonded 1,3-diaza-2-imino heterocyclic ligand (such as an iminoimidazolidine-type ligand) and anionic ligands and a catalyst activator coupound.

18 Claims, No Drawings

OLEFIN POLYMERIZATION CATALYST COMPONENT AND CATALYST SYSTEM AND POLYMERIZATION PROCESS USING SUCH A CATALYST SYSTEM

CROSS-REFERENCE TO RELATED APPLICATION

This application is a continuation of PCT-application PCT/NL/01/00179 filed on 5 Mar. 2001, the disclosure thereof being incorporated by reference

INTRODUCTION

The invention relates to a catalyst component and a catalyst system for the polymerization of an α-olefin, which catalyst component comprises a compound of formula $CyLMZ_p$, wherein
M is a group 4–6 metal,
Cy is a cyclic ligand, having a delocalized π-bond with M,
L is a ketimide ligand,
Z is an anionic ligand, and
p is the number of anionic ligands.

BACKGROUND

As is well known, various processes and catalysts exist for the homopolymerization or copolymerization of α-olefins. For many applications it is of primary importance for a polyolefin to have a high molecular weight while having a relatively narrow molecular weight distribution. It is further desirable to have a catalyst, which within reasonable ranges of ethylene to α-olefin monomer ratios, will catalyze the incorporation of higher (up to 50% by weight) contents of α-olefin comonomers in the production of ethylene-α-olefins copolymers.

Japanese patent application JP6080683 describes unbridged monocyclopentadienyl group 4–6 metal compounds, which are said to provide benefits for propylene polymerization, and exemplifies the production of atactic polypropylene with cyclopentadienyl bistrimethylsilylamide titanium dichloride, activated with methylalumoxane at 40° C.

U.S. Pat. No. 5,625,016 discloses catalyst systems based on an unbridged monocyclopentadienyl group 4 metal compound having a bulky group 15 ligand, which is suitable for the preparation of ethylene-α-olefin copolymers of high molecular weight at high temperatures in solution, with ready incorporation of α-olefins. Examples of ethylene-propylene copolymerization at 115° C. with cyclopentadienyl bis-trimethylsilylamide titanium dimethyl/dimethylanilinium tetra(perfluorophenyl)borate show polymers with up to 30% by weight propylene incorporation, but in a low yield.

U.S. Pat. No. 6,063,879 describes a class of (unbridged) monocyclopentadienyl group 4 metal phosphinimides. Such complexes are suitable for ethylene homo and ethylene-α-olefin copolymerization by solution or gasphase polymerization at high temperature.

Further, U.S. Pat. No. 6,114,481, which represents the most relevant prior art document, discloses a class of group 4 methyl compounds having a ketimide ligand as catalyst component for the preparation of polymers of high molecular weight and low density. More specifically the catalyst comprises a metallocene compound of formula $CyLMZ_2$, wherein M is a group 4 metal, L is a ketimide ligand, (a ketimide group is a group having formula —N=C<), Cy is a cyclic ligand, having a delocalized π-bond with the group 4 metal, such as a cyclopentadienyl group, and two activation reactive ligands Z.

The ketimide ligand L of this known compound contains two bulky carbyl substituents:

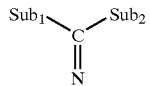

wherein $Sub_1$ and $Sub_2$ are preferably tert.butyl groups.

Ketimide titanium complexes were already prepared by Latham et al., (J. Chem. Soc., Dalton Trans. 1986, 377), but not tested in an olefin polymerization process.

Zhang et al., (J. Am. Chem. Soc., 2000, 122, 5499–5509) studied the thermal stability of dialkyls of the Cp(L)Ti fragment (wherein Cp is a cyclopentadienyl group and L is a ketimide ligand of formula $N=CRR^1$), activated by $B(C_6F_5)_3$.

THE INVENTION

The present invention provides an improved catalyst component and a catalyst system for the α-olefin polymerization, preferably in a solution process, more preferably a high temperature solution process, which give substantially higher activities in, for example, ethylene or α-olefin homopolymerization and ethylene-α-olefin copolymerization processes, compared with prior art ketimide catalyst components, associated with reasonable higher thermal stability. Moreover, they show a low sensitivity for scavengers.

More specifically, the invention relates in a first aspect to a catalyst component for the polymerization of an α-olefin comprising a compound of formula $CyLMZ_p$, wherein
M is a group 4–6 metal,
Cy is a cyclic ligand, having a delocalized π-bond with M,
L is a ketimide ligand,
Z is an anionic ligand, and
p is the number of anionic ligands,
which component is characterized in that
L is an 1,3-diaza-2-imino heterocyclic ligand of formula

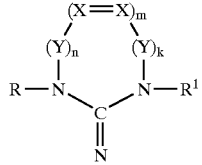

wherein:
each Y is $CRR^1$, $C=CRR^1$, $C=NR$, $SiRR^1$, $C=O$, NR, PR, O, or S
each X is CR, N, or P,
R and $R^1$ are independently selected from hydrogen, hydrocarbyl, silyl or germyl residues, being substituted or not with one or more halogen, amido, phosphido, alkoxy, or aryloxy radicals,
k=0, 1, 2, 3
m=0, 1, 2, 3
n=0, 1, 2, 3, provided that
k+m+n>0,
each Z is independently an anionic ligand selected from halide, hydride, substituted or unsubstituted hydrocarbyl, alkoxide, aryloxide, amide or phosphide; or both Z together form an alkylidene or an arylene residue. Expediently, Z is a mono- or dianionic ligand.

It is observed that the term hydrocarbyl is herein meant to comprise aliphatic and aromatic groups, such as for example phenyl, benzyl, etc.

Said ligand L is thus a monohapto bonded 1,3-diaza-2-imino heterocyclic ligand. The group 4–6 metal M is, preferably, a group 4 metal, such as Ti, Zr or Hf. When M is a group 4 metal, p is 1 or 2.

Suitable examples of metals from group 5 and group 6 of the Periodic Table are V, Nb, Ta and Cr, Mo, W, respectively, in which cases p is 1, 2 or 3, depending upon group Z and the valency of M.

In the above formula, Cy is expediently a cyclopentadienyl, indenyl or fluorenyl ring, which is substituted or not with one to five (cyclopentadienyl), one to seven (indenyl) or one to nine (fluorenyl) substituent R groups, each substituent group R having the above-mentioned meanings.

Examples of alkylidene or arylene residues Z are as follows:

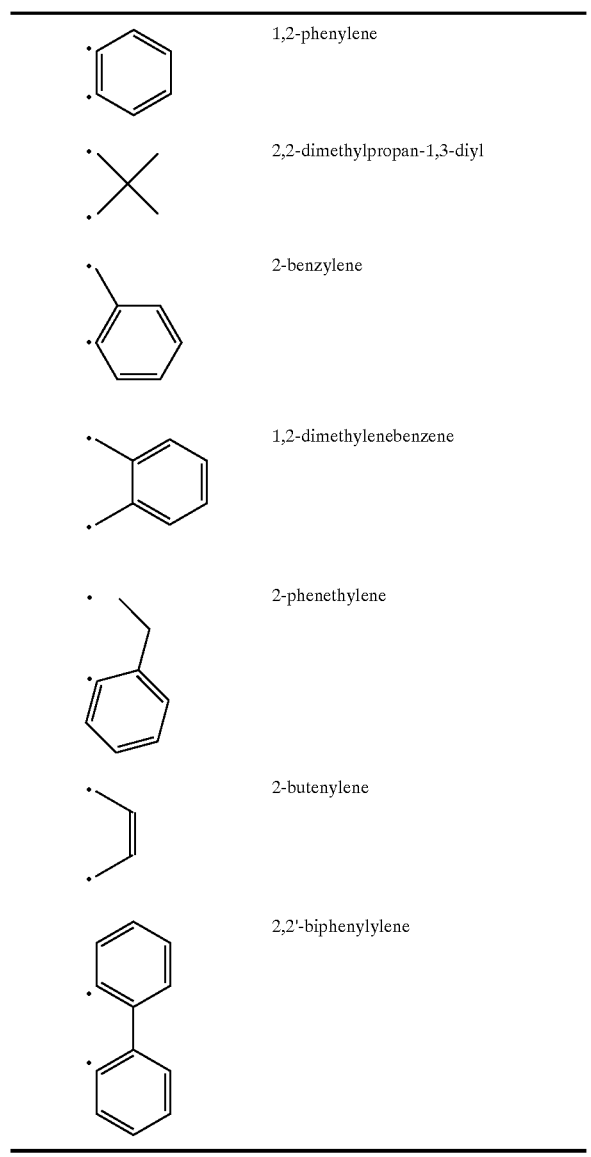

1,2-phenylene 2,2-dimethylpropan-1,3-diyl 2-benzylene 1,2-dimethylenebenzene 2-phenethylene 2-butenylene 2,2'-biphenylylene The present catalyst components, when used in α-olefin polymerization processes, yield a polymer having consistently high molecular weight averages, even at high polymerization temperatures (up to 150° C.), and narrow molecular weight distributions, as appears from the polydispersity values given in the Examples. In ethylene/α-olefin copolymerization processes, the use of the present catalyst components yields ethylene-α-olefin copolymers having high comonomer contents, i.e. up to 50% by weight α-olefin comonomer content.

The preferred catalyst component according to the invention contains a group L, wherein m=0 (zero), n=k=1, Y=CH$_2$, and R=R$^1$=2,6-dimethylphenyl, and is thus a 1,3-bis-2,6-dimethylphenyl-2-iminoimidazolidine ligand.

The present catalyst component is in a preferred embodiment supported on a carrier. This carrier consists expediently either of a metal halide or oxide, which metal oxide can be selected from the group consisting of alumina, boria, magnesia, thoria, zirconia, silica, or mixtures thereof, or it consists of a polymeric material. The preferred carrier material is silica.

The invention relates in a further aspect to a catalyst system comprising the combination of a catalyst component according to the invention with at least one catalyst activator.

Said activator is preferably a Lewis acid; a Brönsted acid or a salt, comprising a cation capable of donating a proton, associated with a substantially non-coordinating anion; a trialkylaluminium; an alkylalumoxane or a combination thereof. Preferably, said activator is B(C$_6$F$_5$)$_3$ or a B(C$_6$F$_5$)$_4$ compound or methylalumoxane, known in the art as BF$_{15}$, BF$_{20}$ or MAO, respectively.

The term "non-coordinating anion" as used herein is meant to indicate activators, which do not, or only weakly, coordinate to the cationic form of the present catalyst component.

The present catalyst system is preferably used in a solution process for the (co-)polymerization of one or more (α-olefins having 2 to 8 carbon atoms at a temperature in the range from 30 to 250° C. and at a pressure in the range from 0.1 to 30 MPa. Said (co-)-polymerization process can nevertheless also be carried out in a slurry process, or in the gas phase and at a temperature from 50–150° C. The temperature used in the polymerization process is preferably at least 80° C. As appears from the following Examples, a high productivity can be obtained, even at high temperatures.

A scavenger can also be used. In this respect, it is observed that a scavenger is in the art normally used to scavenge impurities from the polymerization medium. Examples of suitable scavengers are aluminium alkyls, preferably i-Bu$_3$Al or (i-Bu$_2$Al)$_2$O, and oligomers thereof such as [(i-Bu$_2$Al)$_2$O]$_n$ (n=1, 2, 3).

The use of a scavenger in a solution polymerization process according to the invention appears to result in a high productivity (see the Examples). The catalyst components of the invention are, according to these results, less sensitive for impurities.

The invention also relates to a process, as indicated above, for the copolymerization of at least one α-olefin and at least one alkadiene. Examples of alkadienes are isoprene, 1,5-hexadiene, 1,7-octadiene, 4-vinyl-1-cyclohexene, 1,2,4-trivinylcyclohexane, 5-vinyl-2-norbornene, divinylbenzene, etc.

Instead of butadienes also the use of two equivalents of an olefin or an alkyne is possible.

The invention will now further be explained by way of the following non-limiting Examples and comparative experiments.

Experimental Section

The following abbreviations are used:

Me—Methyl ($CH_3$)
Et—Ethyl ($CH_3CH_2$)
i-Bu—iso-Butyl ($Me_2CHCH_2$)
t-Bu—tert-Butyl ($Me_3C$)
Bz—Benzyl ($C_6H_5CH_2$)
Cp—Cyclopentadienyl ($C_5H_5$)
($Me_2N)_2C$=NH—1,1,3,3-Tetramethylguanidine
1,3-(2,6-$Me_2C_6H_3)_2C_2H_4N_2C$=NH—1,3-Bis-(2,6-dimethylphenyl)-2-iminoimidazolidine
i-$Bu_3$Al—Tri-iso-butylaluminum (TIBA)
(i-$Bu_2$Al)$_2$O—Di-iso-butylalumoxane
THF—Tetrahydrofuran
i-Pr—iso-Propyl ($Me_2CH$)
n-Bu—normal-Butyl ($CH_3CH_2CH_2CH_2$)
1-Bu-3-(2,6-i-$Pr_2C_6H_3)C_2H_4N_2C$=NH—1-n-Butyl-3-(2,6-di-iso-propylphenyl)-2-iminoimidazolidine
Cp*—Pentamethylcyclopentadienyl ($C_5Me_5$)
Cp'—(1-Methylcyclohexyl)cyclopenta-Dienyl [($CH_2)_5CMeC_5H_4$]
TMA—Trimethylaluminium ($Me_3$Al)
MAO—Methylalumoxane [(MeAlO)$_n$.($Me_3$Al)$_{1/3}$]
MMAO—modified Methylalumoxane
DMAO—TMA free Methylalumoxane [(MeAlO)$_n$]

General Considerations

MAO (5 wt % Al, Akzo Nobel), MMAO (Akzo Nobel) and Isopar (DOW) were used as received.

DMAO was generated by removing all volatiles from MAO (5 wt % Al, Akzo Nobel).

All Examples and comparative experiments were performed under a nitrogen atmosphere using standard Schlenk techniques. Toluene (Aldrich, anhydrous, 99.8%) was passed over columns of $Al_2O_3$ (Fluka), BASF R3-11 supported Cu oxygen scavenger and molecular sieves (Aldrich, 4A). Diethyl ether and THF (Aldrich) were dried over $Al_2O_3$ (Fluka) and the other solvents (Aldrich) were dried over molecular sieves (Aldrich 4A). Ethylene and propylene (AGA polymer grade) were passed over BASF R3-11 supported Cu oxygen scavenger and molecular sieves (Aldrich, 4A). 1-Pentene, 1-hexene and styrene (Acros) were dried over $CaH_2$ and distilled before use. 1,1,3,3-Tetramethylguanidine (Acros), Tri-iso-butylaluminum (Witco) and Tris(partafluorophenyl)boron (Strem) were used as received. For determining of comonomer contents in the ethene-α-olefin copolymers $^{13}$C NMR and/or Infrared spectroscopy were used.

NMR spectra were recorded on Varian Gemini 200 and 300 spectrometers. The $^1$H NMR spectra were referenced to resonances of the residual protons in the deuterated solvents. Chemical shifts (δ) are given relative to tetramethylsilane. Gel permeation chromatography (GPC) analysis was carried out on a Polymer Laboratories Ltd. (PL-GPC210) chromatograph using 1,2,4-trichlorobenzene as the mobile phase at 135° C. The samples were prepared by dissolving the polymer in the mobile phase solvent in an external oven at 0.1% (weight/volume) and were run without filtration. For determining of comonomer contents in the ethene-α-olefin copolymers $^{13}$C NMR spectroscopy was used.

The compounds $CpTiCl_3$ (King, R. B.; Eisch, J. J. *Organomet. Synth.*, 1965, 1, 78), $CpTiBz_3$ (Mena, M.; Pellinghelli, M. A.; Royo, P.; Serrano, R.; Tiripicchio, A. *J. Chem. Soc., Chem. Commun.* 1986, 1119), Cp(t-$Bu_2$C=N)$TiCl_2$ (U.S. Pat. No. 6,114,481), Cp[($Me_2N)_2C$=N]$TiCl_2$ (U.S. Pat. No. 6,114,481), 1,3-(2,6-$Me_2C_6H_3)_2C_2H_4N_2C$=NH and 1-Bu-3-(2,6-i-$Pr_2C_6H_3)C_2H_4N_2C$=NH (Toldy, L.; Zubovics, Z.; Kürti, M.; Schäfer, I.; Egypt Gyo. Gyar. DE 2916140, 1979) were prepared according to the procedure in the relevant document.

The compounds Cp*$TiCl_3$ (Llinas, G. H.; Mena, M.; Palacious, F.; Royo, P.; Serrano, R. *J. Organomet. Chem.* 1988, 340, 37) and Cp'Li (Erker, G.; Nolte, R.; Krüger, C.; Schlund, R.; Benn, R.; Grondey, H.; Mynott, R. *J. Organomet. Chem.* 1989, 364, 119) were prepared according to published procedure.

Di-iso-butylalumoxane was generated in situ by treating TIBA with a ½ equivalent of $H_2O$ in toluene.

Preparation 1

Synthesis of Cp[1,3-(2,6-$Me_2C_6H_3)_2C_2H_4N_2C$=N]$TiBz_2$ (Catalyst Component nr. II, According to the Invention).

Preparation Procedure A a) Synthesis of [1,3-(2,6-$Me_2C_6H_3)_2C_2H_4N_2C$=N]Li The lithiated ligand [1,3-(2,6-$Me_2C_6H_3)_2C_2H_4N_2C$=N]Li was generated in situ as follows: BuLi (4 ml of a 2.5M solution in hexane, Acros) was slowly added to 1,3-(2,6-$Me_2C_6H_3)_2C_2H_4N_2C$=NH (3.00 g, 10 mmol) in THF (50 ml) at −80° C. and warmed to room temperature. The obtained product was used as such in the following step.

b) Synthesis of Cp[1,3-(2,6-$Me_2C_6H_3)_2C_2H_4N_2C$=N]$TiCl_2$ (Catalyst Component nr. I According to the Invention).

The solution of [1,3-(2,6-$Me_2C_6H_3)_2C_2H_4N_2C$=N]Li (3.00 g, 10 mmol), obtained in step a), in THF (50 ml) was added slowly to $CpTiCl_3$ (2.20 g, 10.00 mmol) in THF (30 ml) at −80° C. The reaction mixture was warmed to room temperature and stirred for 2 h and the solvent removed in vacuo. The residue was extracted with boiling toluene (40 ml) and the slurry filtered. Slow cooling to room temperature gave yellow-green crystals, which were filtered off and dried in vacuo.

Yield: 90% (4.30 g). $^1$H NMR (CDCl$_3$, 293 K): 2.51 (s, 12H, $CH_3$), 4.02 (s, 4H, $CH_2$), 5.95 (s, 5H, $C_5H_5$), 7.35 (d, 2H, $J_{HH}$=2.9 Hz, $C_6H_3$), 7.26 (t, 1H, $C_6H_3$).

c) Synthesis of the Title Compound

BzMgBr (13 ml of a 1.45M solution in Et$_2$O) was added to a diethylether solution (50 ml) of Cp[1,3-(2,6-$Me_2C_6H_3)_2C_2H_4N_2C$=N]$TiCl_2$ (4.50 g, 9.45 mmol), obtained as indicated in step b), at −80° C. After the addition was complete, the solution was warmed to room temperature and stirred for 12 h. The solvent was removed in vacuo and the residue was extracted with toluene (50 ml). The slurry was filtered and the filtrate was pumped to dryness to give the pure title product as orange solid. Yield: 81% (4.50 g). $^1$H NMR (THF-d$_8$, 293 K): 1.68 (d, 2H, $J_{HH}$=9.1 Hz, $C_6H_5CH_2$), 1.91 (d, 2H, $C_6H_5CH_2$), 2.53 (s, 12H, $CH_3$), 4.04 (s, 4H, $NCH_2$), 5.08 (s, 5H, $C_5H_5$),), 6.32 (d, 4H, $J_{HH}$=7.0 Hz, $C_6H_5CH_2$), 6.55 (t, 2H, $J_{HH}$=7.3 Hz, $C_6H_5CH_2$), 6.87 (t, 4H, $J_{HH}$=7.7 Hz, $C_6H_5CH_2$), 7.17 (s, br, 6H, $C_6H_3$).

Preparation Procedure B 1,3-(2,6-$Me_2C_6H_3)_2C_2H_4N_2C$=NH (0.50 g, 1.70 mmol) in toluene (20 ml) was added to a solution of $CpTiBz_3$ (0.66 g, 1.70 mmol) in toluene (20 ml). The mixture was warmed to 50° C. and stirred for 2 h. The solvent was pumped off and the residue was recrystallized from boiling hexane to give orange crystals of catalyst component nr. II.

Yield: 90% (0.90 g).

$^1$H NMR (C$_6$D$_6$, 293 K): 2.44 (d, 2H, J$_{HH}$=9.5 Hz, C$_6$H$_5$CH$_2$), 2.60 (d, 2 H, C$_6$H$_5$CH$_2$), 2.62 (s, 12H, CH$_3$), 3.44 (s, 4H, NCH$_2$), 5.73 (s, 5H, C$_5$H$_5$), 6.98 (d, 4H, J$_{HH}$=7.7 Hz, C$_6$H$_5$CH$_2$), 7.16 (t, 2H, J$_{HH}$=7.3 Hz, C$_6$H$_5$CH$_2$), 7.25 (m, br, 6H, C$_6$H$_3$), 7.46 (t, 4H, J$_{HH}$=7.7 Hz, C$_6$H$_5$CH$_2$).

Preparation 2

Synthesis of Cp[1-Bu-3-(2,6-i-Pr$_2$C$_6$H$_3$)C$_2$H$_4$N$_2$C=N]TiCl$_2$ (Catalyst Component nr. III According to the Invention)

a) The lithiated ligand [1-Bu-3-(2,6-i-Pr$_2$C$_2$H$_3$)C$_2$H$_4$N$_2$C=N]Li was generated in situ as follows: BuLi (4 ml of a 2.5M solution in hexane, Acros) was slowly added to 1-Bu-3-(2,6-Pr$_2$C$_6$H$_3$)C$_2$H$_4$N$_2$C=NH (3.08 g, 10 mmol) in THF (50 ml) at −80° C. and warmed to room temperature. The obtained product was used as such in the following step.

b) The solution of [1-Bu-3-(2,6-i-Pr$_2$C$_6$H$_3$)C$_2$H$_4$N$_2$C=N]Li (3.08 g, 10 mmol) in THF (50 ml), as obtained in step a), was added slowly to CpTiCl$_3$ (2.20 g, 10.00 mmol) in THF (30 ml) at −80° C. The reaction mixture was warmed to room temperature and stirred for 2 h and the solvent removed in vacuo. The residue was extracted with boiling toluene (40 ml) and the slurry filtered. Slow cooling to room temperature gave yellow needles, which were filtered off and dried in vacuo. Yield: 80% (3.88 g). $^1$H NMR (CDCl$_3$, 293 K): 0.91 [t, 3H, J$_{HH}$=7.3 Hz, CH$_3$(CH$_2$)$_3$], 1.15 [d, 6H, J$_{HH}$=6.6 Hz, (CH$_3$)$_2$CH], 1.35 [d, 6 H, J$_{HH}$=6.6 Hz, (CH$_3$)$_2$CH], 1.38 [m, 2H, (CH$_3$(CH$_2$)$_3$], 1.56 [m, 2H, (CH$_3$(CH$_2$)$_3$], 2.94 [m, 2H, J$_{HH}$=6.6 Hz, (CH$_3$)$_2$CH)], 3.52 [t, 2H, J$_{HH}$=7.3 Hz, (CH$_3$(CH$_2$)$_3$], 3.64 (m, 4H, NCH$_2$CH$_2$N), 5.93 (s, 5H, C$_5$H$_5$), 7.22 (d, 2H, J$_{HH}$=7.7 Hz, C$_6$H$_3$), 7.36 (t, 1H, C$_6$H$_3$).

Preparation 3

Synthesis of Cp[1-Bu-3-(2,6-i-Pr$_2$C$_6$H$_3$)C$_2$H$_4$N$_2$C=N]TiBz$_2$ (Catalyst Component nr. IV, According to the Invention)

A procedure analogous to that employed for preparing catalyst component nr. II (preparation procedure A), was used starting from Cp[1-Bu-3-(2,6-i-Pr$_2$C$_6$H$_3$)C$_2$H$_4$N$_2$C=N]TiCl$_2$ (0.80 g, 1.65 mmol) and BzMgBr (1.65 ml of a 2.0M solution in Et$_2$O). The toluene filtrate was pumped to dryness to give the pure product as red oil. Yield: 90% (0.88 g).

$^1$H NMR (C$_6$D$_6$, 293 K): 0.82 [t, 3H, J$_{HH}$=7.0 Hz, CH$_3$(CH$_2$)$_3$], 1.08 [d, 6 H, J$_{HH}$=6.8 Hz, (CH$_3$)$_2$CH], 1.20 [m, 4H, (CH$_3$(CH$_2$)$_3$], 1.24 [d, 6H, J$_{HH}$=6.8 Hz, (CH$_3$)$_2$CH], 2.33 (d, 2H, J$_{HH}$=9.3 Hz, C$_6$H$_5$CH$_2$), 2.68 (d, 2 H, J$_{HH}$=9.3 Hz, C$_6$H$_5$CH$_2$), 2.87 [t, 2H, J$_{HH}$=8.0 Hz, (CH$_3$(CH$_2$)$_3$], 3.02 [m, 2H, J$_{HH}$=6.8 Hz, (CH$_3$)$_2$CH], 3.12 (m, 4H, NCH$_2$CH$_2$N), 5.60 (s, 5 H, C$_5$H$_5$), 6.84 (d, 4H, J$_{HH}$=7.7 Hz, C$_6$H$_5$CH$_2$), 6.90 (t, 2H, J$_{HH}$=7.3 Hz, C$_6$H$_5$CH$_2$), 7.02 (d, 2H, J$_{HH}$=7.7 Hz, C$_6$H$_3$), 7.08 (t, 1H, C$_6$H$_3$), 7.15 (t, 4H, J$_{HH}$=7.7 Hz, C$_6$H$_5$CH$_2$).

Preparation 4

Synthesis of Cp[(Me$_2$N)$_2$C=N)]TiBz$_2$ (Comparative Catalyst Component A, According to Preparation Procedure A)

A procedure analogous to that employed for preparing catalyst component nr. II (procedure A) was used starting from Cp[(Me$_2$N)$_2$C=N)]TiCl$_2$ (1.06 g, 3.63 mmol) and BzMgBr (6.6 ml of a 1.10M solution in Et$_2$O). Compound A was recrystallized from boiling hexane to give orange crystals. Yield: 74% (1.10 g). $^1$H NMR (toluene-d$_8$, 213 K): 2.31 (s, 12H, CH$_3$), 2.60 (d, 2H, J$_{HH}$=9.5 Hz, C$_6$H$_5$CH$_2$), 2.69 (d, 2H, C$_6$H$_5$CH$_2$), 5.83 (s, 5H, C$_5$H$_5$), 6.92 (t, 2H, J$_{HH}$=7.3 Hz, C$_6$H$_5$CH$_2$), 6.99 (d, 4H, J$_{HH}$=7.3 Hz, C$_6$H$_5$CH$_2$), 7.21 (t, 4H, J$_{HH}$=7.7 Hz, C$_6$H$_5$CH$_2$).

Preparation 5

Synthesis of Cp[(Me$_2$N)$_2$C=N)]TiBz$_2$ (Comparative Catalyst Component A, According to Preparation Procedure B)

A procedure analogous to that employed for preparing catalyst component nr. II (procedure B) was used starting from CpTiBz$_3$ (2.20 g, 5.70 mmol) and (Me$_2$N)$_2$C=NH (0.91 g, 5.7 mmol). Compound A was recrystallized from boiling hexane to give orange crystals. Yield: 81% (1.89 g). $^1$H NMR (C$_6$D$_6$, 293 K): 2.33 (s, 12H, CH$_3$), 2.68 (s, 4H, C$_6$H$_5$CH$_2$), 5.88 (s, 5H, C$_5$H$_5$), 6.91 (t, 2H, J$_{HH}$=7.3 Hz, C$_6$H$_5$CH$_2$), 7.02 (d, 4H, J$_{HH}$=7.3 Hz, C$_6$H$_5$CH$_2$), 7.20 (t, 4H, J$_{HH}$=7.7 Hz, C$_6$H$_5$CH$_2$).

Preparation 6

Synthesis of Cp(t-Bu$_2$C=N)TiBz$_2$ (Comparative Catalyst Component B, According to U.S. Pat. No. 6,114,481)

A procedure analogous to that employed for preparing catalyst component nr. II (procedure A) was used starting from Cp(t-Bu$_2$C=N))TiCl$_2$ (1.90 g, 5.86 mmol) and BzMgBr (10.65 ml of a 1.1M solution in Et$_2$O). The toluene filtrate was pumped to dryness to give the pure product as red-orange oil. Yield: 90% (2.30 g). $^1$H NMR (C$_6$D$_6$, 293 K): 1.11 (s, 18H, CH$_3$), 2.53 (d, 2H, J$_{HH}$=9.9 Hz, C$_6$H$_5$CH$_2$), 2.58 (d, 2H, C$_6$H$_5$CH$_2$), 5.80 (s, 5H, C$_5$H$_5$), 6.90 (t, 2H, J$_{HH}$=8.0 Hz, C$_6$H$_5$CH$_2$), 6.98 (d, 4H, J$_{HH}$=8.0 Hz, C$_6$H$_5$CH$_2$), 7.20 (t, 4H, C$_6$H$_5$CH$_2$).

Preparation 7

Synthesis of Catalyst Components with Cyclometallated Residues

Preparation Procedure C

A procedure analogous to that employed for preparing catalyst component nr. IV (preparation procedure A) can be used, starting from equimolar amounts of a di-Grignard reagent and CyLMZ$_p$ (Z=Cl, Br; p=2 when M=Ti, Zr, V(IV); p=3 when M=Ta, Nb).

Instead of a di-Grignard reagent also magnesacarbocycles and di-lithium, di-sodium, di-potassium or di-zinc halido reagents can be used.

For the synthesis of magnesacarbocycles or di-Grignard reagents see: Wakefield, B. J. *Organomagnesium Methods in Organic Synthesis*, Academic Press, London, 1995, and Goedhijt, M. S. PhD. Thesis, Vrije Universiteit, Amsterdam, 1996.

Preparation Procedure D

An alternative route is the reduction of CyLMZ$_p$ (wherein Z, M and p have the meanings, mentioned above in procedure C) with magnesium in presence of equimolar amounts of a butadiene.

Instead of magnesium also sodium, sodium amalgam, zinc and other reducing agents can be used.

Preparation 8
Synthesis of Cp'[1,3-(2,6-Me$_2$C$_6$H$_3$)$_2$C$_2$H$_4$N$_2$C=N]TiBz$_2$ (Catalyst Component nr. V According to the Invention)

a) Synthesis of (1-methylcyclohexyl)cyclopentadienyltrimethylsilane

Trimethylchlorsilane (29.1 g, 268 mmol) was slowly added to a solution of (1-methyl-cyclohexyl)cyclopentadienyllithium (43.34 g, 258 mmol) in THF (350 ml). After refluxing the mixture for 3,5 h, the solvent was removed in vacuo and the residue was distilled under reduced pressure to give (1-methylcyclohexyl)cyclopentadienyltrimethylsilane as yellow oil.

Yield: 57% (34.36 g). $^1$H NMR (CDCl$_3$, 293 K): 0.12 (s, 9H, (CH$_3$)$_3$Si), 1.07 (s, 3H, CH$_3$C), 1.39–1.80 (m, 10H, (CH$_2$)$_5$), 3.23 (s, 1H, C$_5$H$_4$), 6.06 (d, 1H, C$_5$H$_4$), 6.43 (m, 1H, C$_5$H$_4$), 6.58 (d, 1H, C$_5$H$_4$).

b) Synthesis of Cp'TiCl$_3$

TiCl$_4$ (9.18 g, 48 mmol) was added to a solution of Cp'SiMe$_3$ (11.25 g, 48 mmol) in toluene (150 ml), obtained as indicated in step a), at 0° C. After the addition was complete, the solution was warmed to room temperature and stirred for 2 d. The volatiles were removed in vacuo and the residue was recrystallized from toluene (40 ml), to give orange crystals, which were filtered off and dried in vacuo.

Yield: 56% (8.49 g). $^1$H NMR (CDCl$_3$, 293 K) 1.15 (m, 2H, (CH$_2$)$_5$), 1.30 (s, 3H, CH$_3$C), 1.48 (m, 4H, (CH$_2$)$_5$), 1.63 (m, 4H, (CH$_2$)$_5$), 6.76 (t, 2H, J$_{HH}$=2.9 Hz, C$_5$H$_4$), 6.97 (t, 2H, C$_5$H$_4$).

c) Synthesis of Cp'TiBz$_3$

BzMgBr (17.4 ml of a 1.63M solution in Et$_2$O) was added to a diethylether solution (100 ml) of Cp'TiCl$_3$ (2.95 g, 9.35 mmol), obtained as indicated in step b), at 0° C. After the addition was complete, the solution was warmed to room temperature and stirred for 12 h. The solvent was removed in vacuo, the residue extracted with hexane (50 ml) and the slurry filtered. Slow cooling to −30° C., gave dark red crystals, which were filtered off and dried in vacuo. Yield: 62% (2.81 g). $^1$H NMR (C$_6$D$_6$, 293 K): 0.99 (s, 3H, CH$_3$C), 1.09 (m, 2H, (CH$_2$)$_5$), 1.38 (m, 8H, (CH$_2$)$_5$), 3.05 (s, 6H, C$_6$H$_5$CH$_2$), 5.59 (t, 2H, J$_{HH}$=2.6 Hz, C$_5$H$_4$), 5.80 (t, 2H, C$_5$H$_4$), 6.89 (d, 6H, J$_{HH}$=7.4 Hz, C$_6$H$_5$CH$_2$), 6.91 (t, 3H, J$_{HH}$=7.3 Hz, C$_6$H$_5$CH$_2$), 7.18 (t, 6H, J$_{HH}$=7.7 Hz, C$_6$H$_5$CH$_2$).

d) Synthesis of the Title Compound

A procedure analogous to that employed for preparing catalyst component nr. II (procedure B) was used starting from Cp'TiBz$_3$ (0.70 g, 1.45 mmol) and 1,3-(2,6-Me$_2$C$_6$H$_3$)$_2$C$_2$H$_4$N$_2$C=NH (0.41 g, 1.41 mmol). Catalyst component nr. V was recrystallized from boiling hexane to give orange crystals. Yield: 88% (0.85 g).). $^1$H NMR (C$_6$D$_6$, 293 K): 0.96 (s, 3H, CH$_3$C), 1.20–1.60 (m, 10H, (CH$_2$)$_5$), 2.41 (d, 2H, J$_{HH}$=9.5 Hz, C$_6$H$_5$CH$_2$), 2.46 (d, 2H, C$_6$H$_5$CH$_2$), 2.52 (s, 12H, CH$_3$), 3.30 (s, 4H, NCH$_2$), 5.61 (t, 2H, J$_{HH}$=2.6 Hz, C$_5$H$_4$), 5.88 (t, 2H, C$_5$H$_4$), 6.85 (d, 4H, J$_{HH}$=7.4 Hz, C$_6$H$_5$CH$_2$), 7.00 (t, 2H, J$_{HH}$=7.3 Hz, C$_6$H$_5$CH$_2$), 7.15 (m, br, 6H, C$_6$H$_3$), 7.18 (t, 4H, J$_{HH}$=7.7 Hz, C$_6$H$_5$CH$_2$).

Preparation 9
Synthesis of Cp*[1,3-(2,6-Me$_2$C$_6$H$_3$)$_2$C$_2$H$_4$N$_2$C=N]TiCl$_2$ (Catalyst Component nr. VI According to the Invention)

A procedure analogous to that employed for preparing catalyst component nr. I was used starting from Cp*TiCl$_3$ (1.30 g, 4.50 mmol) and 1,3-(2,6-Me$_2$C$_6$H$_3$)$_2$C$_2$H$_4$N$_2$C=NLi (1.35 g, 4.50 mmol). Catalyst component nr. VI was recrystallized from boiling toluene to give olive-green crystals. Yield: 73% (1.80 g).). $^1$H NMR (CDCl$_3$, 293 K): 1.69 (s, 15H, (CH$_3$)$_5$C$_5$), 2.48 (s, 12H, CH$_3$), 3.92 (s, 4H, NCH$_2$), 7.10 (m, br, 6H, C$_6$H$_3$).

Comparative Experiments a–h

The catalyst components A and B were prepared as indicated.

Polymerization of Ethylene (Without Scavenger)

Polymerization experiments were conducted in a 500 ml autoclave reactor at different temperatures in the batch mode. The results are given in Table 1.

The Following Procedure was Used:

The reactor was charged with 190 ml of purified toluene and stirred at 600 rpm. 10 ml of a 0.0011 molar toluene solution of B(C$_6$F$_5$)$_3$ was added and the reactor was heated to reach the desired temperature. Ethylene was added to reach 0.5 MPa total pressure. Then 10 ml of a 0.001 molar toluene solution of the catalyst component was injected. Ethylene was continuously added to the reactor to maintain the pressure constant.

TABLE 1

| experiment | Catalyst Component | T ° C. | P$_{total}$ MPa | t$_{run}$ min | m$_{pol.}$*g | productivity gmol$^{-1}$h$^{-1}$Pa$^{-1}$ | Mw | Mw/Mn |
|---|---|---|---|---|---|---|---|---|
| A | A | 30 | 0.5 | 15 | 7.2 | 5.76 | 1,009,600 | 1.40 |
| B | A | 50 | 0.2 | 15 | 2.3 | 4.60 | 367,250 | 1.71 |
| C | A | 80 | 0.5 | 15 | 3.0 | 2.40 | | |
| d$^a$ | A | 100 | 0.5 | 15 | — | — | | |
| e | B | 30 | 0.5 | 15 | 5.8 | 4.64 | | |
| f | B | 50 | 0.5 | 15 | 4.9 | 3.92 | | |
| g | B | 80 | 0.5 | 15 | 4.4 | 3.52 | | |
| h | B | 100 | 0.5 | 15 | 3.5 | 2.80 | | |

$^a$The catalytic system was found to be inactive under the applied conditions.

*m$_{pol}$ is the obtained mass of the produced polymer.

EXAMPLES 1–10

The polymerisation of ethylene according to comparative experiments a–h was repeated, but now by using catalyst components according to the invention, catalyst component nr. II and nr IV respectively.

The results are given in Table 2.

TABLE 2

| Example nr. | Catalyst Component nr. | T °C. | $P_{total}$ Mpa | $t_{run}$ min | $m_{pol}$.g | productivity $gmol^{-1}h^{-1}Pa^{-1}$ | Mw | Mw/Mn |
|---|---|---|---|---|---|---|---|---|
| 1 | II | 30 | 0.5 | 15 | 7.1 | 5.68 | 713,650 | 1.94 |
| 2 | II | 50 | 0.5 | 15 | 17.9 | 14.32 | | |
| 3 | II | 80 | 0.5 | 15 | 11.2 | 8.96 | 361,000 | 1.91 |
| 4 | II | 100 | 0.5 | 15 | 8.5 | 6.80 | 255,000 | 2.09 |
| 5 | II | 130 | 0.5 | 5 | 3.5 | 8.40 | | |
| 6 | IV | 30 | 0.5 | 15 | 6.5 | 5.20 | | |
| 7 | IV | 50 | 0.5 | 15 | 15.6 | 12.48 | 560,850 | 1.87 |
| 8 | IV | 80 | 0.5 | 15 | 13.6 | 10.88 | | |
| 9 | IV | 100 | 0.5 | 15 | 8.8 | 7.04 | 291,500 | 1.91 |
| 10 | IV | 120 | 0.5 | 15 | 7.8 | 6.24 | 210,950 | 1.91 |

As appears from the test results given in the Tables 1 and 2, the prior art catalyst components A or B can, in an ethylene polymerization process, only expediently be used at a temperature of at most about 80° C. A catalyst system according to the invention (comprising catalyst components II or IV) can, on the other hand, be used at a higher temperature, such as a temperature of 100° C. or 130° C., at which temperatures still a high productivity is obtained. This implies that the catalyst system is still stable at such high temperatures. It is observed that Example nr. 5 was only carried out for 5 minutes.

The results also show that narrow molecular weight distributions of from 1.0–2.5 are obtained by using a catalyst system according to the invention.

Comparative Experiments i–l
Polymerization of Ethylene (with Scavenger)

Polymerization runs were conducted in a 1000 ml autoclave reactor at a temperature of 80° C. in the batch mode. The following procedure was used:

The reactor was charged with 240 ml of purified toluene and stirred at 600 rpm. 10 ml of a 0.02 molar toluene solution of scavenger was added and the reactor was heated to reach the temperature of 80° C. Ethylene was added to reach 0.5 MPa total pressure. Then 10 ml of a 0.001 molar toluene solution of the catalyst component/activator (Ti/B $(C_6F_5)_3$ ratio of 1:1.1) was injected. Ethylene was continuously added to the reactor to maintain the total pressure constant. Scavenger S1 consisted of i-$Bu_3Al$, scavenger S2 consisted of (i-$Bu_2Al)_2O$.

TABLE 3

| Experiment | catalyst component | scavenger | T °C. | $P_{total}$ MPa | $t_{run}$ min | $m_{pol}$.g | Productivity $gmol^{-1}h^{-1}Pa^{-1}$ | Mw | Mw/Mn |
|---|---|---|---|---|---|---|---|---|---|
| i[a] | A | S1 | 80 | 0.5 | 15 | — | — | | |
| j[a] | A | S2 | 80 | 0.5 | 15 | — | — | | |
| k | B | S1 | 80 | 0.5 | 15 | 6.4 | 5.12 | | |
| l | B | S2 | 80 | 0.5 | 15 | 5.8 | 4.64 | | |

[a]The catalytic system was found to be inactive under the applied conditions.

EXAMPLES 11–15

The polymerization of ethylene according to comparative experiments i–l was repeated, but now by using catalyst systems according to the invention, comprising catalyst components nr. II and IV respectively, but in the presence of the same scavengers S1 and S2.

The results are given in Table 4.

TABLE 4

| Example nr. | Catalyst Component Nr. | scavenger | T °C. | $P_{total}$ Mpa | $t_{run}$ min | $m_{pol}$.g | Productivity $gmol^{-1}h^{-1}Pa^{-1}$ | Mw | Mw/Mn |
|---|---|---|---|---|---|---|---|---|---|
| 11 | II | S1 | 80 | 0.5 | 15 | 8.1 | 6.48 | 547,350 | 1.70 |
| 12 | II | S2 | 80 | 0.5 | 15 | 20.0 | 16.00 | | |
| 13 | IV | S1 | 125 | 0.5 | 15 | 7.9 | 9.48 | 271,500 | 1.71 |
| 14 | IV | S2 | 80 | 0.5 | 15 | 20.5 | 16.40 | 532,300 | 1.74 |
| 15 | IV | S2 | 125 | 0.5 | 15 | 13.5 | 10.80 | 283,850 | 1.85 |

The results given in the Tables 3 and 4 show the beneficial effect of a scavenger to the catalyst systems of the invention as appears from the high productivity data of the polymerization process according to the invention, carried out at a temperature of 80° C.

Comparative Experiments m–o
Polymerization of Propylene

The polymerization experiments were conducted in a 500 ml autoclave reactor at different temperatures (Table 5) in the batch mode. The following procedure was used:

The reactor was charged with 190 ml of purified toluene and stirred at 600 rpm. 10 ml of a 0.0011 molar toluene solution of $B(C_6F_5)_3$ was added and the reactor was heated to reach the desired temperature. Propylene was added to reach 0.3 MPa total pressure. Then 10 ml of a 0.001 molar toluene solution of the catalyst component was injected. Propylene was continuously added to the reactor to maintain the total pressure constant.

TABLE 5

| Experiment | Catalyst Component | T °C. | $p_{total}$ MPa | $t_{run}$ min | $m_{pol}.g$ | Productivity kgmol$^{-1}$h$^{-1}$ | Mw | Mw/Mn |
|---|---|---|---|---|---|---|---|---|
| M | A | 30 | 0.3 | 15 | 12.8 | 5,120 | 710,800 | 1.56 |
| N | A | 50 | 0.3 | 15 | 4.6 | 1,840 | 356,000 | 1.60 |
| O[a] | A | 80 | 0.3 | 15 | — | — | | |

[a]The catalyst system was found to be inactive under the applied conditions.

EXAMPLES 16–18

The polymerization of propylene according to comparative experiments m–o was repeated, but now by using a catalyst system according to the invention.

The results are given in Table 6.

TABLE 6

| Example nr. | catalyst component nr. | T °C. | $p_{total}$ MPa | $t_{run}$ min | $m_{pol}.g$ | Productivity kgmol$^{-1}$h$^{-1}$ | Mw | Mw/Mn |
|---|---|---|---|---|---|---|---|---|
| 16 | II | 30 | 0.3 | 15 | 36.7 | 14,680 | 112,050 | 2.01 |
| 17 | II | 50 | 0.3 | 15 | 35.9 | 14,360 | 81,400 | 1.93 |
| 18 | II | 80 | 0.3 | 15 | 16.8 | 6,720 | 38,900 | 1.68 |

The obtained productivity data clearly show the better catalytic activity of a catalyst system of the invention, compared with a prior art catalyst system. The narrow molecular weight distributions to be obtained when using a catalyst system of the invention are shown.

EXAMPLES 19–24
Copolymerization of Ethylene with an α-olefin

The polymerizations were conducted in a 500 ml (1000 ml with scavenger) autoclave reactor at a temperature of 80° C. in the batch mode. The following procedure was used: The reactor was charged with 210 ml (240 ml) of purified toluene and stirred at 600 rpm. 20 ml of the desired α-olefin and 10 ml of a 0.02 molar toluene solution of scavenger (1000 ml autoclave) were added and reactor was heated to reach the temperature of 80° C. Ethylene was added to reach 0.5 MPa total pressure. Then 10 ml of a 0.001 molar toluene solution of the catalyst component/activator (Ti/B($C_6F_5$)$_3$ ratio of 1/1.1) was injected. Ethylene was continuously added to the reactor to maintain the total pressure constant.

The results are given in Table 7.

TABLE 7

| Example nr. | Catalyst Component nr. | T °C. | α-olefin | $t_{run}$ min | $m_{pol}.g$ | Productivity kgmol$^{-1}$h$^{-1}$ | α-olefin incorporation wt % | Mw | Mw/Mn |
|---|---|---|---|---|---|---|---|---|---|
| 19[a] | II | 80 | propene | 15 | 31.9 | 12,760 | | 130,600 | 1.95 |
| 20[a] | II | 80 | pentene-1 | 15 | 28.2 | 11,280 | ~20 | 206,350 | 1.90 |
| 21 | II | 80 | hexene-1 | 15 | 9.9 | 3,960 | 18.4 | 181,400 | 1.98 |
| 22[a] | II | 80 | hexene-1 | 15 | 21.5 | 8,600 | | 212,000 | 1.85 |
| 23 | II | 80 | styrene | 15 | 4.9 | 1,960 | 10.3 | 178,600 | 2.06 |
| 24 | II | 50 | isoprene | 15 | 24.0 | 9,600 | | 136,750 | 2.78 |

[a]260 ml toluene solvent; 0.2 mmol i-Bu$_3$Al.

The above test results show that a catalyst component according to the invention, together with B(C$_6$F$_5$)$_3$ as a co-catalyst, used in a copolymerization process in solution at a high temperature of 80° C., catalyzes the incorporation of up to 20% by weight of different α-olefin comonomers in the production of ethylene-α-olefin copolymers.

EXAMPLES 25–31

Copolymerization of Ethylene with 1-octene in Presence of Hydrogen

The polymerizations were conducted in a 3000 ml autoclave reactor at a temperature of 130° C. in the batch mode. The following procedure was used:

The reactor was charged with 263 ml of 1-octene and Isopar was added to reach 1500 ml of total volume. The reactor was heated to reach the temperature of 130° C. and the desired amount of hydrogen was added. Ethylene was added to reach 3.0 MPa total pressure. Then 2 ml of MMAO (toluene solution, 0.1 molar in Al) and 0.5 ml of a 0.005 molar toluene solution of the catalyst component nr. V/activator (Ti/B(C$_6$F$_5$)$_3$ ratio of 1:1.2) were injected. Ethylene was continuously added to the reactor to maintain the pressure constant and the ethylene uptake was measured.

TABLE 8

| Example Nr. | Catalyst Component nr. | hydrogen ml | Al/Ti | C$_2$ uptake ml | productivity Kg (PE)/g (Ti) | Mw | Mw/Mn | 1-octene incorporation mol % |
|---|---|---|---|---|---|---|---|---|
| 25 | V | 487 | 40 | 42 | 351 | 16100 | 3.01 | 2.84 |
| 26 | V | 328 | 40 | 52 | 435 | 24000 | 2.33 | 3.09 |
| 27 | V | 278 | 40 | 47 | 393 | 26000 | 2.43 | 2.88 |
| 28[a] | V | 227 | 80 | 30 | 253 | 29700 | 2.34 | 2.98 |
| 29[a] | V | 227 | 80 | 58 | 481 | 31200 | 2.29 | 3.02 |
| 30[a] | V | 177 | 80 | 69 | 576 | 34900 | 2.42 | 2.95 |
| 31[a] | V | 128 | 80 | 63 | 526 | 40400 | 2.08 | 3.06 |

[a]4 ml MMAO was added.

The above test results show that the molecular weight of the copolymer yielded from a catalyst component according to the invention, together with B(C$_6$F$_5$)$_3$ as a co-catalyst, used in a solution polymerization process at a high temperature of 130° C., can be determined by different amounts of hydrogen.

EXAMPLES 32–36

Polymerization of Ethylene with MAO as Activator

The polymerizations were conducted in a 1000 ml autoclave reactor at a temperature of 100° C. in the batch mode. The following procedure was used:

The reactor was charged with 240 ml of purified toluene and stirred at 600 rpm. The desired amount of activator in 10 ml of toluene was added and the reactor was heated to reach the temperature of 100° C. Ethylene was added to reach 0.5 MPa total pressure. Then the desired amount of catalyst component nr. VI in 10 ml of toluene was injected. Ethylene was continuously added to the reactor to maintain the pressure constant.

TABLE 9

| Example | Catalyst μmol | activator | Al/Ti | t$_{run}$ Min | m$_{pol.}$ | productivity gmol$^{-1}$h$^{-1}$Pa$^{-1}$ | Mw | Mw/Mn |
|---|---|---|---|---|---|---|---|---|
| 32 | 2 | MAO | 500 | 15 | 2.3 | 9.20 | 1012000 | 1.9 |
| 33 | 10 | DMAO | 500 | 15 | 19.4 | 15.52 | 404800 | 2.1 |
| 34 | 2 | DMAO | 500 | 15 | 12.7 | 50.80 | 985600 | 2.0 |
| 35 | 0.2 | DMAO | 1000 | 15 | 4.2 | 168.00 | 1499000 | 2.0 |
| 36 | 0.05 | DMAO | 4000 | 15 | 4.6 | 736.00 | 1349000 | 1.9 |

The results given in Table 9 show that a catalyst component according to the invention, together with DMAO as activator, used in a solution polymerization process at a high temperature of 100° C., gives a highly active catalyst system which produces high molecular weight polyethylene.

What is claimed is:

1. In a catalyst component for the polymerization of an α-olefin comprising a compound of formula CyLMZ$_p$, wherein
   M is a group 4–6 metal,
   Cy is a cyclic ligand, having a delocalized π-bond with M,
   L is a ketimide ligand,
   Z is an anionic ligand, and
   p is the number of anionic ligands the improvement wherein
   L is an 1,3-diaza-2-imino heterocyclic ligand of

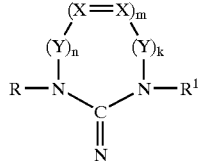

wherein:
   each Y is CRR$^1$, C=CRR$^1$, C=NR, SiRR$^1$, C=O,NR, PR, O, or S
   each X is CR, N, or P,
   R and R$^1$ are independently selected from hydrogen, hydrocarbyl, silyl or germyl residues, being substituted or not with one or more halogen, amido, phosphido, alkoxy, or aryloxy radicals,
   k=0, 1, 2, 3
   m=0, 1, 2, 3
   n=0, 1, 2, 3, provided that
   k+m+n>0,
   each Z is independently an anionic ligand selected from halide, hydride, substituted or unsubstituted hydrocarbyl, alkoxide, aryloxide, amide or phosphide; or both Z together form an alkylidene or an arylene residue.

2. A catalyst component according to claim 1, wherein in said group L:
m=0,
n=k=1,
Y=CH$_2$, and
R=R$^1$=2,6-dimethyiphenyl.

3. A catalyst component according to claim 1, wherein said M is titanium.

4. A catalyst component according to claim 1, wherein Cy is a cyclopentadienyl ligand.

5. A catalyst component according to claim 1 wherein each of Z is a benzyl group.

6. A catalyst component according to claim 1, wherein said catalyst component is supported on a carrier.

7. A catalyst component according to claim 6, wherein said carrier is a metal halide or oxide.

8. A catalyst component according to claim 7, wherein said metal oxide is selected from the group consisting of alumina, boria, magnesia, thoria, zirconia, silica, or mixtures thereof.

9. A catalyst component according to claim 6, wherein said carrier is a polymeric material.

10. A catalyst system for the polymerisation of at least one α-olefin comprising a catalyst component according to claim 1, wherein said catalyst component is provided with at least one catalyst activator.

11. A catalyst system according to claim 10, wherein said activator is a Lewis acid; a Brönsted acid or a salt comprising a cation capable of donating a proton, associated with a substantially non-coordinating anion; a trialkylaluminium; an alkylalumoxane or a combination thereof.

12. A catalyst system according to claim 11 wherein said activator is B(C$_6$F$_5$)$_3$, a B(C$_6$F$_5$)$_4$ compound or methylalumoxane.

13. A process for the (co-) polymerization of at least one α-olefin having 2 to 8 carbon atoms at a temperature from 30 to 250° C. by effecting the (co-)polymerization at a pressure of from 0.1 to 30 Pa and in the presence of a catalyst component or system according to claim 1.

14. A process according to claim 13, wherein said process is carried out in solution or slurry.

15. A process according to claim 13, wherein said process is carried out in the gas phase and at a temperature from 50–150° C.

16. A process according to claim 13, wherein said process is carried out in the presence of a scavenger.

17. A process according to claim 16, wherein said scavenger is i-Bu$_3$Al and (i-Bu$_2$Al)$_2$O or oligomers thereof.

18. A process according to claim 13, wherein at least one α-olefin and at least one alkadiene are copolymerized.

* * * * *